United States Patent [19]
Ascione

[11] Patent Number: 5,955,061
[45] Date of Patent: Sep. 21, 1999

[54] COSMETIC FILTER COMPOSITIONS CONTAINING DIBENZOYLMETHANE, ALKYL β, β'-DIPHENYLACRYLATE AND BENZOTRIAZOLE SILICONE, AND USES THEREOF

[75] Inventor: Jean-Marc Ascione, Hoboken, N.J.

[73] Assignee: L'Oreal, France

[21] Appl. No.: 08/973,117

[22] PCT Filed: Apr. 3, 1997

[86] PCT No.: PCT/FR97/00606

§ 371 Date: Dec. 5, 1997

§ 102(e) Date: Dec. 5, 1997

[87] PCT Pub. No.: WO97/37634

PCT Pub. Date: Oct. 16, 1997

[30] Foreign Application Priority Data

Apr. 5, 1996 [FR] France .................................. 96 04360

[51] Int. Cl.⁶ .............................. A61K 7/42; A61K 7/44; A61K 7/00
[52] U.S. Cl. .............................. 424/59; 424/60; 424/400; 424/401
[58] Field of Search .............................. 424/89, 60, 400, 424/401

[56] References Cited

U.S. PATENT DOCUMENTS

| | | | |
|---|---|---|---|
| 3,220,972 | 11/1965 | Lamoreaux | 528/15 |
| 3,697,473 | 10/1972 | Polmanteer et al. | 524/862 |
| 4,340,709 | 7/1982 | Jeram et al. | 528/15 |
| 5,089,250 | 2/1992 | Forestier et al. | 424/43 |
| 5,576,354 | 11/1996 | Deflandre et al. | 514/685 |
| 5,587,150 | 12/1996 | Deflandre et al. | 424/59 |
| 5,618,520 | 4/1997 | Hansenne et al. | 424/59 |

*Primary Examiner*—Shelley A. Dodson
*Attorney, Agent, or Firm*—Finnegan, Henderson, Farabow, Garrett & Dunner, L.L.P.

[57] ABSTRACT

The present invention relates to novel cosmetic compositions comprising, in a cosmetically acceptable vehicle, at least one dibenzoylmethane derivative, at least one alkyl β,β'-diphenylacrylate derivative and at least one specific benzotriazole silicone. By virtue of a synergy effect between these three screening agents, these compositions have improved sun protection factors.

The invention also relates to the use of these compositions in the cosmetic field.

22 Claims, No Drawings

COSMETIC FILTER COMPOSITIONS CONTAINING DIBENZOYLMETHANE, ALKYL β, β'-DIPHENYLACRYLATE AND BENZOTRIAZOLE SILICONE, AND USES THEREOF

The present invention relates to novel cosmetic compositions which are more particularly intended for the photoprotection of the skin and/or the hair against ultraviolet radiation (compositions referred to hereinbelow more simply as antisun compositions), as well as to their use in the abovementioned cosmetic application. More precisely, the invention relates to novel cosmetic compositions having an improved sun protection factor and comprising, in a cosmetically acceptable support, at least one dibenzoylmethane derivative, at least one alkyl β,β'-diphenylacrylate and at least one specific benzotriazole silicone.

It is known that light radiation with wavelengths of between 280 nm and 400 nm permits tanning of the human epidermis, and that light rays with wavelengths of between 280 nm and 320 nm, known as UV-B rays, cause skin burns and erythema which may be harmful to the development of a natural tan; this UV-B radiation should thus be screened out.

It is also known that UV-A rays, with wavelengths of between 320 nm and 400 nm, which cause tanning of the skin, are liable to induce an adverse change in the latter, especially in the case of sensitive skin or of skin which is continually exposed to solar radiation. UV-A rays cause in particular a loss of elasticity of the skin and the appearance of wrinkles, leading to premature skin ageing. They promote triggering of the erythemal reaction or amplify this reaction in certain individuals and may even be the cause of phototoxic or photoallergic reactions. It is thus desirable also to screen out UV-A radiation.

Many compounds intended for the photoprotection (UV-A and/or UV-B) of the skin have been proposed to date.

These antisun compositions are quite often in the form of an emulsion of oil-in-water type (that is to say a cosmetically acceptable vehicle consisting of a continuous aqueous dispersing phase and a discontinuous oily dispersed phase) which contains, in various concentrations, one or more conventional lipophilic and/or hydrophilic organic screening agents which are capable of selectively absorbing harmful UV radiation, these screening agents (and their amounts) being selected as a function of the desired sun protection factor (SPF) which is expressed mathematically by the ratio of the irradiation time necessary to reach the erythema-forming threshold with the UV screening agent to the time necessary to reach the erythema-forming threshold without UV screening agent.

After considerable research conducted in the abovementioned field of photoprotection, the Applicant has discovered, surprisingly and unexpectedly, that a combination of three specific families of screening compounds which are already known per se in the prior art makes it possible, on account of a synergy effect, to obtain antisun compositions having markedly improved sun protection factors.

This discovery forms the basis of the present invention.

Thus, in accordance with one of the subjects of the present invention, novel cosmetic compositions, in particular antisun compositions, are now proposed, characterized in that they comprise, in a cosmetically acceptable vehicle, i) at least one dibenzoylmethane derivative as first screening agent, ii) at least one alkyl β,β'-diphenylacrylate derivative as second screening agent, and iii) at least one benzotriazole silicone corresponding to one of the following formulae:

$$B-\underset{R}{\overset{R}{\underset{|}{Si}}}-O-\left[\underset{R}{\overset{R}{\underset{|}{Si}}}-O\right]_r\left[\underset{A}{\overset{R}{\underset{|}{Si}}}-O\right]_s\underset{R}{\overset{R}{\underset{|}{Si}}}-B \quad (1)$$

or $$\left[\underset{R}{\overset{R}{\underset{|}{Si}}}-O\right]_t\left[\underset{A}{\overset{R}{\underset{|}{Si}}}-O\right]_u \quad (2)$$

in which formulae (1) and (2):

R, which may be identical or different, are chosen from $C_1$–$C_{10}$ alkyl, phenyl, 3,3,3-trifluoropropyl and trimethylsilyloxy radicals, at least 80%, on a number basis, of the radicals R being methyl, B, which may be identical or different, are chosen from the radicals P, and the radical A, r is an integer from 0 to 50 inclusive and s is an integer from 0 to 20 inclusive, and if s=0, at least one of the two symbols B denotes A, u is an integer from 1 to 6 inclusive and t is an integer from 0 to 10 inclusive, it being understood that t+u is equal to or greater than 3, and the symbol A denotes a monovalent radical linked directly to a silicon atom, and which corresponds to formula (3) below:

$$\left[\begin{array}{c}\text{[benzotriazole-phenol structure]}\end{array}\right]\begin{array}{l}-(Y)_n\\-(X)_m-(CH_2)_p-\underset{Z}{\overset{|}{CH}}-CH_2-\end{array} \quad (3)$$

in which formula (3):

Y, which may be identical or different, are chosen from $C_1$–$C_8$ alkyl radicals, halogens and $C_1$–$C_4$ alkoxy radicals, it being understood that, in this latter case, two adjacent Y groups on the same aromatic ring may together form an alkylidenedioxy group in which the alkylidene group contains 1 or 2 carbon atoms, X represents O or NH, Z represents hydrogen or a $C_1$–$C_4$ alkyl radical, n is an integer from 0 to 3 inclusive, m is 0 or 1, p represents an integer from 1 to 10 inclusive, as third screening agent.

The subject of the present invention is also a cosmetic treatment process for protecting the skin and/or the hair against UV radiation, in particular solar radiation, characterized in that it consists in applying thereto an effective amount of a cosmetic composition as defined above.

Other characteristics, aspects and advantages of the present invention will become apparent on reading the detailed description which follows.

A first essential screening agent (referred to hereinbelow as screening agent A) for the compositions according to the invention is a dibenzoylmethane derivative. Dibenzoylmethane derivatives are products which are already well known per se as agents for screening UV-A radiation and are described in particular in the documents FR-A-2,326,405, FR-A-2,440,933 and EP-A-0,114,607, the teachings of which documents are, as regards the actual definition of these products, entirely included in the present description by way of reference.

Among the dibenzoylmethane derivatives towards which the present invention is more particularly directed, mention may be made in particular, in a non-limiting manner, of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Among the abovementioned dibenzoylmethane derivatives, it is most particularly preferred, according to the present invention, to use 4-tertbutyl-4'-methoxydibenzoylmethane, in particular that placed on sale under the trade name "Parsol 1789" by the company Givaudan, this screening agent corresponding to the structural formula (I) below:

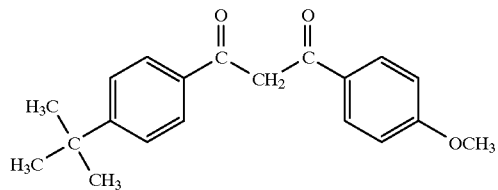

(I)

Another preferred dibenzoylmethane derivative according to the present invention is 4-isopropyldibenzoylmethane, this screening agent being sold under the name "Eusolex 8020" by the company Merck, and corresponding to the structural formula (II) below:

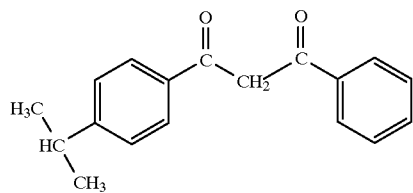

(II)

The dibenzoylmethane derivative may be present in the compositions in accordance with the invention at a content of from 0.1% to 8%, preferably from 0.2% to 5% by weight relative to the total weight of the composition.

A second essential screening agent (referred to hereinbelow as screening agent B) for the compositions of the invention is an alkyl β,β'-diphenylacrylate. Among the β,β'-diphenylacrylate derivatives which can be used according to the present invention, mention may be made of 2-ethylhexyl α-cyano-β,β'-diphenylacrylate or ethyl α-cyano-β,β'-diphenylacrylate.

2-Ethylhexyl α-cyano-β,β'-diphenylacrylate, also known as octocrylene, is a liquid lipophilic screening agent which is already known per se for its UV-B activity. This is a product which is commercially available and is sold in particular under the name "Uvinul N 539" from the company BASF. This compound corresponds to formula (III) below:

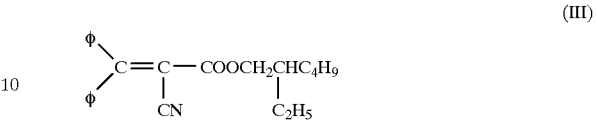

(III)

in which φ denotes a phenyl radical.

Ethyl α-cyano-β,β'-diphenylacrylate, also known as etocrylene, is a screening agent which is also known per se for its UV-B activity. This is a product which is commercially available and is sold in particular under the name "Uvinul N 35" by the company BASF. This compound corresponds to formula (IV) below:

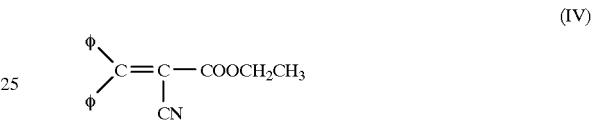

(IV)

in which φ denotes a phenyl radical.

More generally, the alkyl β,β'-diphenylacrylates which can be used in the context of the present invention are those already described in European patent EP-A-0,514,491, the teaching of which is, in this respect, entirely included in the present application. It will be noted that the abovementioned document EP-A-0,514,491 teaches that alkyl β,β'-diphenylacrylate derivatives make it possible to photochemically stabilize the dibenzoylmethane derivatives in order to guarantee, for this binary combination, constant protection over time, in particular during prolonged exposure. However, this document neither describes nor suggests at all the synergy effect associated with the ternary combination in accordance with the invention as regards the initial intrinsic SPFs.

Preferably, the alkyl β,β'-diphenylacrylate derivative is present in the compositions according to the invention at a content of from 0.1% to 20% by weight relative to the total weight of the composition. More preferably, this content is from 0.2% to 15% by weight relative to the total weight of the composition.

A third essential screening agent (referred to hereinbelow as screening agent C) for the compositions in accordance with the present invention is a specific benzotriazole silicone. The specific benzotriazole silicones used in the context of the present invention are selected from the known general family of benzotriazole silicones, and are those which correspond to the following formulae:

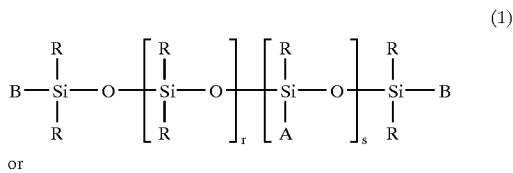

(1)

or

-continued

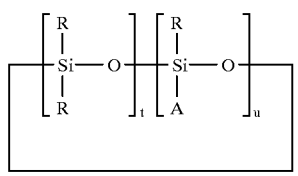
(2)

in which formulae (1) and (2):

R, which may be identical or different, are chosen from $C_1$–$C_{10}$ alkyl, phenyl, 3,3,3-trifluoropropyl and trimethylsilyloxy radicals, at least 80%, on a number basis, of the radicals R being methyl, B, which may be identical or different, are chosen from the radicals R and the radical A, r is an integer from 0 to 50 inclusive and s is an integer from 0 to 20 inclusive, and if s=0, at least one of two symbols B denotes A, u is an integer from 1 to 6 inclusive and t is an integer from 0 to 10 inclusive, it being understood that t+u is equal to or greater than 3, and the symbol A denotes a monovalent radical linked directly to a silicon atom, and which corresponds to Formula (3) below:

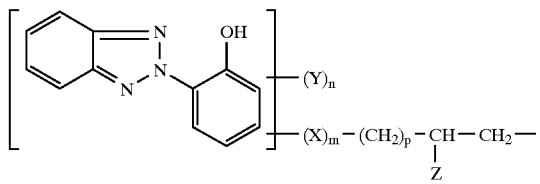
(3)

in which formula (3):

Y, which may be identical or different, are chosen from $C_1$–$C_8$ alkyl radicals, halogens and $C_1$–$C_4$ alkoxy radicals, it being understood that, in this latter case, two adjacent Y groups on the same aromatic ring may together form an alkylidenedioxy group in which the alkylidene group contains 1 or 2 carbon atoms, X represents O or NH, Z represents hydrogen or a $C_1$–$C_4$ alkyl radical, n is an integer from 0 to 3 inclusive, m is 0 or 1, p represents an integer from 1 to 10 inclusive.

As emerges from formula (3) given above, attachment of the chain unit —$(X)_m$—$(CH_2)_p$—CH(Z)—CH$_2$— to the benzotriazole unit, which thus ensures connection of the said benzotriazole unit to the silicon atom or the silicone chain, may take place, according to the present invention, in all the available positions offered by the two aromatic rings of the benzotriazole:

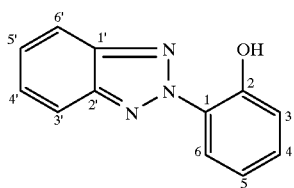

Preferably, this attachment takes place in position 3, 4, 5 (aromatic ring bearing the hydroxyl function) or 4' (benzene ring adjacent to the triazole ring), and even more preferably in position 3, 4 or 5. In a preferred embodiment of the invention, the attachment takes place in position 3.

Similarly, attachment of the substituent unit or units Y may take place in all the other available positions in the benzotriazole. However, preferably, this attachment takes place in position 3, 4, 4', 5 and/or 6. In a preferred embodiment of the invention, attachment of the unit Y takes place in position 5.

In formulae (1) and (2) above, the alkyl radicals may be linear or branched and chosen in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R according to the invention are methyl, ethyl, propyl, n-butyl, n-octyl and 2-ethylhexyl radicals. Even more preferably, the radicals R are all methyl radicals.

Among the compounds of formula (1) or (2) above, it is preferred to use those corresponding to formula (1), that is to say diorganosiloxanes containing a short linear chain.

Among the compounds of formula (1) above, it is preferred to use those for which the radicals B are both radicals R.

Among the linear diorganosiloxanes falling within the scope of the present invention, random derivatives or well-defined block derivatives having at least one, and preferably all, of the following characteristics:

B is a radical R,

R is alkyl and even more preferably is methyl, r is from 0 to 15 inclusive; s is from 1 to 10 inclusive, n is non-zero and preferably equal to 1, and Y is then chosen from methyl, tert-butyl and $C_1$–$C_4$ alkoxy, Z is hydrogen or methyl, m=0 or [m=1 and X=O]

p is equal to 1 are more particularly preferred.

One family of compounds which is particularly suitable for the invention is that defined by the general formula (4) below:

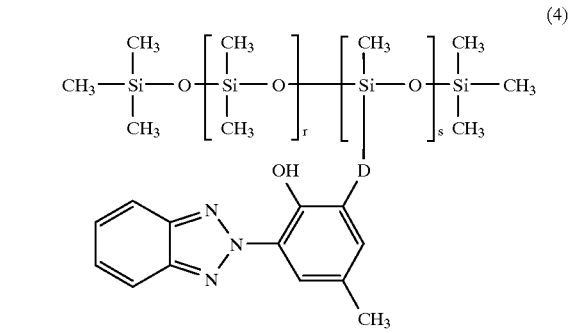
(4)

with $0 \leq r \leq 10$, $1 \leq s \leq 10$, and where D represents the divalent radical:

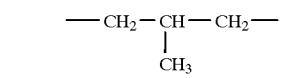

In a particularly preferred embodiment of the invention, the benzotriazole silicone is the compound (referred to as compound (c) in the rest of the text) corresponding to the following formula:

compound (c)

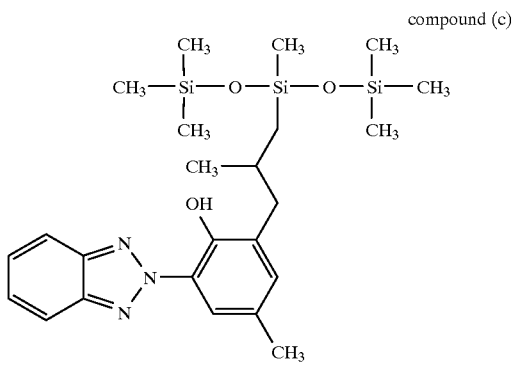

To prepare the silicone screening agents of formulae (1) and (2), the process may be carried out conventionally using a hydrosilylation reaction (namely

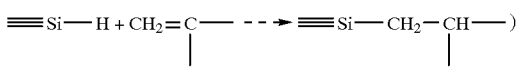

starting with the corresponding silicone in which, for example, all the radicals A are hydrogen atoms. This starting silicone is referred to hereinbelow as SiH-containing derivative. These SiH-containing derivatives are products which are well known in the silicone industry and are generally commercially available. They are described, for example, in the American patents U.S. Pat. No. 3,220,972, U.S. Pat. No. 3,697,473 and U.S. Pat. No. 4,340,709.

This SiH-containing derivative may therefore be represented either by formula (1b) below:

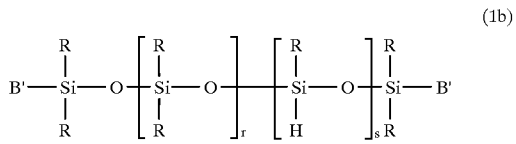

in which R, r and s have the meaning given above for formula (1), and the radicals B', which may be identical or different, are chosen from the radicals R and a hydrogen atom, or by formula (2b) below:

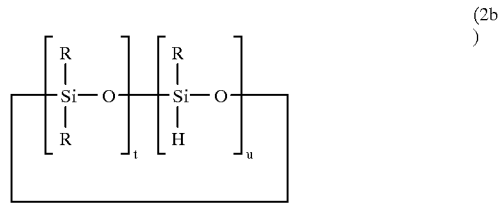

in which R, t and u have the meaning given above for formula (2).

A standard hydrosilylation reaction is thus carried out on this SiH-containing derivative of formula (1b) or (2b), this reaction being carried out in the presence of a catalytically effective amount of a platinum catalyst, on an organic benzotriazole derivative of formula (3b) below:

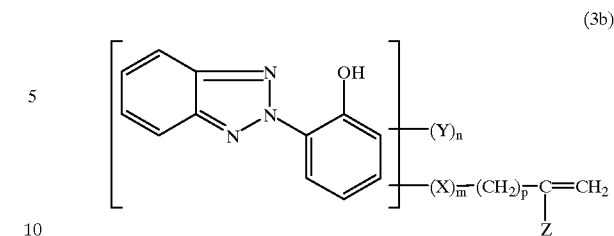

in which Y, X, Z, n, m and p have the meaning given above for formula (3).

Processes which are suitable for the preparation of the products of formula (3b) above are described in particular in U.S. Pat. Nos. 4,316,033 and 4,328,346.

In addition, the details of the operating conditions to follow to carry out the hydrosilylation reaction between the compounds of formula (1b) or (2b) above and the compound of formula (3b) above are given in patent application EP-0, 392,883, the teaching of which is, in this respect, entirely included in the present description by way of reference.

In the compositions of the invention, from 0.1 to 15% by weight, preferably from 0.2 to 10% by weight, of a benzotriazole silicone as defined above relative to the total weight of the composition is generally used.

From a practical point of view, the above three screening agents A, B and C are, obviously, preferably all present in the final composition in respective proportions chosen such that the synergy effect, as regards the sun protection factor imparted by the resulting combination, is optimal. The exact range of the weight ratios [screening agent A/screening agent B/screening agent C] in which this optimal synergy effect is effectively achieved may vary slightly depending on the total amount of screening agents A, B and C used.

In a particularly preferred embodiment of the invention, the weight ratio [screening agent A/screening agent B/screening agent C] is 1/1/1.

The antisun cosmetic compositions according to the invention may, obviously, contain one or more hydrophilic or lipophilic UVA- and/ or UVB-active complementary sunscreens (absorbers) other than, of course, the three screening agents mentioned above. These complementary screening agents may be chosen in particular from cinnamic derivatives, salicylic derivatives, camphor derivatives, triazine derivatives, benzophenone derivatives and p-aminobenzoic acid derivatives.

The compositions according to the invention may also contain agents for the artificial tanning and/or browning of the skin (self-tanning agents) such as, for example, dihydroxyacetone (DHA).

The cosmetic compositions according to the invention may also contain pigments or nanopigments (average size of the primary particles: generally between 5 nm and 100 nm, preferably between 10 nm and 50 nm) of coated or uncoated metal oxides, for example nanopigments of titanium oxide (amorphous or crystallized in rutile and/or anatase form), of iron oxide, of zinc oxide, of zirconium oxide or of cerium oxide which are all UV-photoprotective agents that are well known per se. Standard coating agents are, moreover, alumina and/or aluminium stearate. Such coated or uncoated metal oxide nanopigments are described in particular i n patent applications EP-A-0,518,772 and EP-A-0,518,773.

The compositions of the invention may also comprise standard cosmetic adjuvants chosen in particular from fatty substances, organic solvents, ionic or nonionic thickeners, softeners, antioxidants, opacifying agents, stabilizers, emolients, silicones, α-hydroxy acids, anti-foaming agents, moisturizers, vitamins, fragrances, preserving agents, surfactants, fillers, sequestering agents, polymers, propellants, basifying or acidifying agents, dyes or any other ingredient usually used in cosmetics, in particular for the manufacture of antisun compositions in the form of emulsions.

The fatty substances may consist of an oil or a wax or mixtures thereof, and they also comprise fatty acids, fatty alcohols and fatty acid esters. The oils may be chosen from animal, plant, mineral or synthetic oils and in particular from liquid petrolatum, liquid paraffin, volatile or non-volatile silicone oils, isoparaffins, poly-α-olefins, fluoro oils and perfluoro oils. Similarly, the waxes may be chosen from animal, fossil, plant, mineral or synthetic waxes that are known per se.

Among the organic solvents, mention may be made of lower alcohols and polyols.

The thickeners may be chosen in particular from crosslinked polyacrylic acids and modified or unmodified guar gums and cellulose gums such as hydroxypropyl guar gum, methylhydroxyethylcellulose, hydroxypropylmethylcellulose or hydroxyethylcellulose.

Obviously, a person skilled in the art will take care to select the optional complementary compound or compounds mentioned above and/or the amounts thereof such that the advantageous properties intrinsically associated with the ternary combination in accordance with the invention are not, or are substantially not, adversely affected by the addition or additions envisaged.

The compositions with which the invention is concerned may be prepared according to techniques which are well known to those skilled in the art, in particular those intended for the preparation of emulsions of oil-in-water or water-in-oil type.

This composition may be, in particular, in simple or complex emulsion form (O/W, W/O, O/W/O or W/O/W), such as a cream, a milk, a gel or a cream-gel, a powder or a solid stick and may optionally be packaged as an aerosol and may be in the form of a foam or a spray.

Preferably, this composition is in the form of an oil-in-water emulsion.

When the composition is an emulsion, the aqueous phase thereof may comprise a nonionic vesicle dispersion prepared according to known processes (Bangham, Standish and Watkins, J. Mol. Biol. 13, 238 (1965), FR-2,315,991 and FR-2,416,008).

The cosmetic composition of the invention may be used as a composition for protecting human skin or the hair against ultraviolet rays, as an antisun composition or as a make-up product.

When the cosmetic composition according to the invention is used for protecting human skin against UV rays or as an antisun composition, it may be in the form of a suspension or dispersion in solvents or in fatty substances, in the form of a nonionic vesicle dispersion or alternatively in the form of an emulsion, preferably of oil-in-water type, such as a cream or a milk, or in the form of an ointment, a gel, a cream-gel, a solid stick, a stick, an aerosol foam or a spray.

When the cosmetic composition according to the invention is used to protect the hair, it may be in the form of a shampoo, a lotion, a gel, an emulsion, a nonionic vesicle dispersion or a lacquer for the hair and may constitute, for example, a rinse-out composition to be applied before or after shampooing, before or after dyeing or bleaching, before, during or after permanent-waving or straightening of the hair, a styling or treating lotion or gel, a blow-drying or hair-setting lotion or gel or a composition for permanent-waving, straightening, dyeing or bleaching the hair.

When the composition is used as a make-up product for the eyelashes, the eyebrows or the skin, such as a skin treatment cream, a foundation, a lipstick, an eyeshadow, a blusher, a mascara or an eyeliner, it may be in anhydrous or aqueous, solid or pasty form, for instance oil-in-water or water-in-oil emulsions, nonionic vesicle dispersions or suspensions.

As a guide, for the antisun formulations in accordance with the invention which have a vehicle of oil-in-water emulsion type, the aqueous phase (in particular comprising the hydrophilic screening agents) generally represents from 50 to 95% by weight, preferably from 70 to 90% by weight, relative to the whole formulation, the oily phase (in particular comprising the lipophilic screening agents) from 5 to 50% by weight, preferably from 10 to 30% by weight, relative to the whole formulation, and the (co)emulsifying agent(s) from 0.5 to 20% by weight, preferably from 2 to 10% by weight, relative to the whole formulation.

Concrete, but in no way limiting, examples illustrating the invention will now be given.

EXAMPLE 1

Various antisun formulations in the form of an oil-in-water type emulsion were prepared containing (the amounts are expressed in % by weight relative to the total weight of the composition):

| | |
|---|---|
| 4-(tert-butyl)-4'-methoxydibenzoylmethane | x % |
| 2-ethylhexyl α-cyano-β,β'-diphenylacrylate | y % |
| benzotriazole silicone (compound (c) as defined above in the description) | z % |
| mixture of cetylstearyl alcohol and cetylstearyl alcohol oxyethylenated with 33 mol of EO (80/20), sold under the name "Sinnowax AO" by Henkel | 7% |
| glyceryl monostearate, sold under the trade name "Géléol Copeaux" by Gattefossé | 2% |
| cetyl alcohol, sold under the name "Lorol C 16" by Henkel | 1.5% |
| 2,2,4,4,6,6,8-heptamethylnonane, sold under the trade name "Isohexadecane" by Bayer | 15% |
| polydimethylsiloxane, sold under the name "Silbione 70 047 V 300" by Rhône-Poulenc | 1.5% |
| glycerol | 20% |
| preserving agents | qs |
| water | qs 100% |

Four emulsions were thus prepared: three comparative emulsions A, B and C, each respectively comprising 4-(tert-butyl)-4'-methoxydibenzoylmethane alone, 2-ethylhexyl α-cyano-β,β'-diphenylacrylate alone and benzotriazole silicone (c) alone, and an emulsion D in accordance with the invention comprising (4-(tert-butyl)-4'-methoxydibenzoylmethane, 2-ethylhexyl α-cyano-β,β'-diphenylacrylate and benzotriazole silicone (c)). The respective amounts of these three screening agents in the four emulsions A, B, C and D are collated in Table (I) below:

TABLE (I)

| Constituent | Formula A (comparative) | Formula B (comparative) | Formula C (comparative) | Formula D (invention) |
|---|---|---|---|---|
| x (%) | 6 | 0 | 0 | 2 |
| y (%) | 0 | 6 | 0 | 2 |
| z (%) | 0 | 0 | 6 | 2 |

For each of these formulations, the sun protection factor (SPF) associated therewith was then determined. This factor was determined using the in vitro method described by B. L. Diffey et al. in J. Soc. Cosmet. Chem. 40-127-133 (1989); this method consists in determining the monochromatic protection factors every 5 nm over a wavelength range from 290 to 400 nm and in calculating the sun protection factor therefrom according to a given mathematical equation.

The results (average value corresponding to three tests) are collated in Table (II) below:

TABLE (II)

| Formula | A (comparative) | B (comparative) | C (comparative) | D (invention) |
|---------|-----------------|-----------------|-----------------|---------------|
| SPF     | 3.6             | 5.0             | 4.8             | 8.5           |

These results clearly show the synergy effect obtained with composition D in accordance with the invention. The SPF of composition D comprising the synergistic mixture of three screening agents (4-(tert-butyl)-4'-methoxydibenzoylmethane, 2-ethylhexyl α-cyano-β,β'-diphenylacrylate and benzotriazole silicone (c)) according to the invention is significantly higher than that of each of the formulae A, B and C which respectively comprise 4-(tert-butyl)4'-methoxydibenzoylmethane alone (formula A), 2-ethylhexyl α-cyano-β,β'-diphenylacrylate alone (formula B) and benzotriazole silicone (c) alone (formula C), with identical overall contents.

EXAMPLE 2

Comparative compositions E, F, G, H, J and K were also prepared, with a common vehicle identical to the emulsions of Example 1 and for which the respective proportions of 4-(tert-butyl)-4'-methoxydibenzoylmethane, 2-ethylhexyl α-cyano-β,β'-diphenylacrylate and benzotriazole silicone (c) are collated in Table (III) below:

TABLE (III)

| Screening Agent | Formula E | Formula F | Formula G | Formula H | Formula J | Formula K |
|-----------------|-----------|-----------|-----------|-----------|-----------|-----------|
| x (%)           | 2         | 0         | 0         | 0         | 2         | 2         |
| y (%)           | 0         | 2         | 0         | 2         | 0         | 2         |
| z (%)           | 0         | 0         | 2         | 2         | 2         | 0         |

For each of these formulations, the sun protection factor was then determined according to the same procedure as that used in Example 1.

The results (average value corresponding to three tests) are collated in Table (IV) below:

TABLE (IV)

| Formula | E   | F   | G   | H   | J   | K   |
|---------|-----|-----|-----|-----|-----|-----|
| SPF     | 3.2 | 2.2 | 2.7 | 3.3 | 4.1 | 4.2 |

Thus, if the SPF obtained for composition H, J or K comprising the two complementary screening agents is added to each SPF obtained above for one of the formulas E, F or G containing only one of the screening agents x, y or z, SPFs are obtained which are markedly lower than the SPF of composition D according to Example 1 of the invention and which comprises the synergistic combination of the three screening agents according to the invention in the same overall proportion of screening agents of 6%. Table (V) below summarizes these values:

TABLE (V)

| SPF (formula E) + SPF (formula H) | SPF (formula F) + SPF (formula J) | SPF (formula G) + SPF (formula K) | SPF (formula D) (invention) |
|---|---|---|---|
| 6.5 | 6.3 | 6.9 | 8.5 |

I claim:

1. A cosmetic composition, said composition comprising, in a cosmetically acceptable vehicle,
   i) at least one dibenzoylmethane derivative as a first screening agent,
   ii) at least one alkyl β,β'-diphenyl-acrylate derivative as a second screening agent, and
   iii) as a third screening agent, at least one benzotriazole silicone having formula (1) or (2):

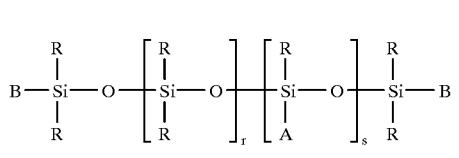

or

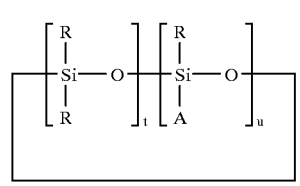

wherein:
R, which may be identical or different, is a $C_1$–$C_{10}$ alkyl, phenyl, 3,3,3-trifluoropropyl or trimethylsilyloxy radical, and at least 80%, on a number basis, of the R radicals present are methyl, B, which may be identical or different, is defined as an R radical or an A radical, r is an integer ranging from 0 to 50 and s is an integer ranging from 0 to 20, with the proviso that if s=0, then at least one of the two B radicals represents an A radical, u is an integer ranging from 1 to 6 and t is an integer ranging from 0 to 10, with the proviso that t+u is equal to or greater than 3, and A represents a monovalent radical linked directly to a silicon atom and having the formula (3):

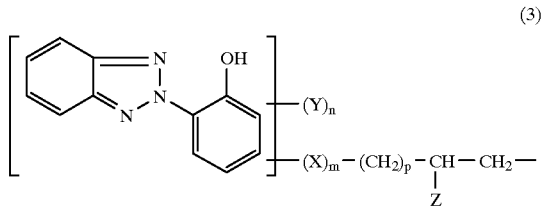

wherein:
Y, which may be identical or different, is a $C_1$–$C_8$ alkyl radical, a halogen or a $C_1$–$C_4$ alkoxy radical, it being understood that when two adjacent Y groups on the same aromatic ring are $C_1$–$C_4$ alkoxy, said Y groups may together form an alkylidenedioxy group wherein the alkylidene group contains 1 or 2 carbon atoms, X represents O or NH, Z represents hydrogen or a $C_1$–$C_4$ alkyl radical, n is an integer ranging from 0 to 3, m is 0 or 1, and p represents an integer ranging from 1 to 10.

2. A composition according to claim 1, wherein said cosmetic composition is an antisun composition.

3. A composition according to claim 1, wherein said at least one dibenzoylmethane derivative is:

2-methyldibenzoylmethane,
4-methyldibenzoylmethane,
4-isopropyidibenzoylmethane,
4-tert-butyldibenzoylmethane,
2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyi-4'-methoxydibenzoylmethane, or
2,6-dimethyl-4-tert-buty-4'-methoxyd ibenzoylmethane.

4. A composition according to claim 3, wherein said at least one dibenzoylmethane derivative is 4-tert-buty-4'-methoxydibenzoylmethane.

5. A composition according to claim 3, wherein said at least one dibenzoylmethane derivative is 4-isopropyldibenzoylmethane.

6. A composition according to claim 1, wherein said at least one dibenzoylmethane derivative is present in said composition in an amount ranging from 0.1% to 8% by weight relative to the total weight of said composition.

7. A composition according to claim 6, wherein said at least one dibenzoylmethane derivative is present in said composition in an amount ranging from 0.2% to 5% by weight relative to the total weight of said composition.

8. A composition according to claim 1, wherein said at least one alkyl β,β'-diphenylacrylate derivative is 2-ethylhexyl α-cyano-β,β'-diphenylacrylate or ethyl α-cyano-β,β'-diphenylacrylate.

9. A composition according to claim 8, wherein said at least one alkyl β,β'-diphenylacrylate derivative is 2-ethylhexyl α-cyano-β,β'-diphenylacrylate.

10. A composition according to claim 1, wherein said at least one alkyl β,β'-diphenylacrylate derivative is present in said composition in an amount ranging from 0.1% to 20% by weight relative to the total weight of said composition.

11. A composition according to claim 10, wherein at least one alkyl β,β'-diphenylacrylate derivative is present in said composition in an amount ranging from 0.2% to 15% by weight relative to the total weight of said composition.

12. A composition according to claim 1, wherein said at least one benzotriazole silicone is a compound of formula (1) wherein the B radicals are defined as the R radicals.

13. A composition according to claim 12, wherein said at least one benzotriazole silicone has at least one of the following characteristics:

R is alkyl, r ranges from 0 to 15 and s ranges from 1 to 10, n is non-zero and Y is methyl, tert-butyl or $C_1$–$C_4$ alkoxy, Z is hydrogen or methyl, m=0 or m=1 while X=O, or p is equal to 1.

14. A composition according to claim 13, wherein R is methyl.

15. A composition according to claim 13, wherein n is equal to 1.

16. A composition according to claim 12, wherein said at least one benzotriazole silicone has all of the following characteristics:

R is alkyl, r ranges from 0 to 15 and s ranges from 1 to 10, n is non-zero and Y is methyl, tert-butyl or $C_1$–$C_4$ alkoxy, Z is hydrogen or methyl, m=0 or m=1 while X=O, and p is equal to 1.

17. A composition according to claim 16, wherein said at least one benzotriazole silicone is a compound of formula (4):

wherein:

$0 \leq r \leq 10$;

$1 \leq s \leq 10$, and

D represents the divalent radical:

—$CH_2$—CH—$CH_2$—.
    |
    $CH_3$

18. A composition according to claim 17, wherein said at least one benzotriazole silicone has the formula (c):

19. A composition according to claim 1, wherein said at least one benzotriazole silicone is present in said composition in an amount ranging from 0.1 to 15% by weight relative to the total weight of said composition.

20. A composition according to claim 19, wherein said at least one benzotriazole silicone is present in said composition in an amount ranging from 0.2 to 10% by weight relative to the total weight of said composition.

21. A cosmetic treatment process for protecting the skin and/or the hair against UV radiation, said process comprising applying to said skin and/or said hair an effective amount of a cosmetic composition according to claim 1.

22. A process according to claim 21, wherein said UV radiation is solar radiation.

* * * * *

UNITED STATES PATENT AND TRADEMARK OFFICE
CERTIFICATE OF CORRECTION

PATENT NO.: 5,955,061

DATED: September 21, 1999

INVENTOR(S): ASCIONE

It is certified that an error appears in the above-identified patent and that said Letters Patent is hereby corrected as shown below:

In claim 3, column 13, line 16, "4-isopropyidibenzoylmethane" should read --4-isopropyldibenzoylmethane--.

In claim 3, column 13, line 27, "methoxyd ibenzoylmethane" should read -- methoxydibenzoylmethane--.

Signed and Sealed this

Twentieth Day of June, 2000

*Attest:*

Q. TODD DICKINSON

*Attesting Officer*     *Director of Patents and Trademarks*